United States Patent [19]

Gutman

[11] 3,981,995
[45] Sept. 21, 1976

[54] PROCESS FOR CONTROL OF SHEEP MAGGOT FLY

[75] Inventor: Arnold D. Gutman, Berkeley, Calif.

[73] Assignee: Stauffer Chemical Company, Westport, Conn.

[22] Filed: Mar. 6, 1975

[21] Appl. No.: 556,049

[52] U.S. Cl. .............................................. 424/219
[51] Int. Cl.² ........................................... A01N 9/36
[58] Field of Search ................................... 424/219

[56] References Cited
UNITED STATES PATENTS 3,780,143   12/1973   Gutman ............................... 424/219

Primary Examiner—V. D. Turner
Attorney, Agent, or Firm—Joel G. Ackerman

[57] ABSTRACT

Sheep maggot fly (*Lucilia sericata* or *L. cuprina*), particularly organophosphorus resistant strains, can be controlled by the application of an effective amount of the compound S-propargyl-O-benzyl, ethylphosphonodithioate

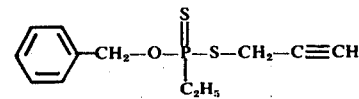

1 Claim, No Drawings

PROCESS FOR CONTROL OF SHEEP MAGGOT FLY

DESCRIPTION OF THE INVENTION

This invention relates to the control of the sheep maggot fly (*Lucilia sericata* or *Lucilia cuprina*), particularly to the larvae thereof, by the external application of a pesticidally effective amount of a substance to sheep. A substantial number of the substances which have been found effective against this parasite are organic phosphates, such as the compound 2-chloro-1-(2,4-dichlorophenyl)-vinyl diethyl phosphate, generically known as chlorfenvinphos. In addition to the usual problems of control of external parasites, at least one strain of *L. cuprina* has developed which has marked resistance to organophosphorus compounds, particularly organic phosphates (hereinafter referred to as "O.P. resistant Q strain").

It has now been discovered that sheep maggot fly (*Lucilia sericata* or *Lucilia cuprina*) can be controlled by external application of an effective amount of the compound S-propargyl-O-benzyl, ethylphosphonodithioate, i.e.

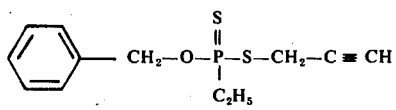

to sheep. (The compound is shown in U.S. Pat. No. 3,780,143.) In general, it is applied in concentrations of from about 0.01% to about 5.0%. More particularly, it has been found that the application of the above compound at a concentration as low as 0.01% produces some protection against normal Lucilia strains, and the application of this compound in a larger amount can provide exceptionally long protection against both normal and O.P. resistant strains of Lucilia larvae. For example, as shown hereinbelow, application at 0.10% concentration produced quite satisfactory protection.

In vitro tests were conducted as follows: Newly hatched normal strain *Lucilia sericata* were introduced into tubes containing the test compound in emulsion or solid dispersion form, mixed with bovine serum. Decreasing concentrations were utilized in the tests, starting at 50 ppm. The minimum lethal concentration (MLC) was observed 72 hours after treatment. Similar tests were conducted against *Lucilia cuprina* (O.P. resistant Q strain) to determine the degree of resistance. The results of these tests showed that the MLC for the subject compound against L. sericata (normal strain) was 0.25 ppm, and against L. cuprina (O.P resistant Q strain) was 2.5 ppm.

Fleece saturation tests were then conducted. A single application of an emulsion was made to a measured and marked area on the back of a single sheep, using solutions containing 0.01% and 0.10% of the compound in an inert solvent. The area was then challenged with larval implants (100–200 *L. sericata* and *L. cuprina* (O.P. resistant Q strain) on the fifth week after treatment and thereafter at weekly intervals until strikes occurred. Results were as follows:

| Concentration applied | Protection from larval strike (weeks) | |
|---|---|---|
| | Normal strain (*L. sericata*) | Q strain (O.P. resistant *L. cuprina*) |
| 0.01% | 8 weeks | Not tested |
| 0.10% | >28 weeks | 28 weeks |

In the case of the 0.10% solution, the tests were terminated after 28 weeks, protection for this period of time being considered quite satisfactory in comparison to chlorfenvinphos, which protects for 21–23 weeks, depending on the challenge and the weather.

PREPARATION 12.4 g (0.05 moles) of ethylthionophosphine sulfide, 10.8 g (0.10 moles) of benzylalcohol and 200 ml of dioxane are combined in a 1-liter beaker and stirred magnetically at room temperature until a solution is obtained. The solution is stirred and cooled in an ice bath. 11.9 g (0.1 moles) of propargylbromide is added, followed by 15.1 g (0.15 moles) of triethylamine added over a period of 10 minutes. The resulting mixture is stirred at room temperature for 1 hour, then poured into 500 ml of benzene and consecutively washed with 200 ml of water, 100 ml of saturated sodium bicarbonate solution, and 2 100 ml portions of water. The benzene phase is dried with anhydrous $MgSO_4$ and evaporated to yield 20.3 g (75.2% of theory) of the desired product $N_D^{30}$ 1.5605.

The compound can be used to treat sheep in the same manner as with other external pesticides. In general, it would be dissolved in an appropriate inert solvent, combined with a suitable wetting agent, and included in an effective amount in a sheep dip treatment in which sheep are to be immersed in a vat or tank, or which is to be sprayed onto sheep in a sheep spray race. The compound can be used alone, or combined in the sheep dip with other pesticides and such other substances as may be required for adequate sheep treatment.

What is claimed is:

1. A process for the control of larvae of *Lucilia sericata* or *Lucilia cuprina* comprising the external application to sheep of an insecticidally effective amount of the compound S-propargyl-O-benzyl, ethylphosphonodithioate.

* * * * *